(12) United States Patent
Ichim et al.

(10) Patent No.: US 11,712,474 B2
(45) Date of Patent: Aug. 1, 2023

(54) REDUCTION OF POST-SURGERY CANCER METASTASIS BY COMBINATION OF CANNABIDIOL AND NR2F6 INHIBITION

(71) Applicant: Regen Biopharma, Inc., Medina, MN (US)

(72) Inventors: Thomas Ichim, San Diego, CA (US); David Koos, La Mesa, CA (US)

(73) Assignee: Regen Biopharma, Inc., La Mesa, CA (US)

( * ) Notice: Subject to any disclaimer, the term of this patent is extended or adjusted under 35 U.S.C. 154(b) by 210 days.

(21) Appl. No.: 17/037,284

(22) Filed: Sep. 29, 2020

(65) Prior Publication Data

US 2021/0353755 A1      Nov. 18, 2021

Related U.S. Application Data

(60) Provisional application No. 62/885,740, filed on Aug. 12, 2019.

(51) Int. Cl.

| | |
|---|---|
| *A61K 45/06* | (2006.01) |
| *A61K 9/00* | (2006.01) |
| *A61K 31/352* | (2006.01) |
| *C12Q 1/6811* | (2018.01) |
| *A61K 31/05* | (2006.01) |
| *A61K 31/7088* | (2006.01) |
| *A61K 31/7105* | (2006.01) |
| *A61K 31/713* | (2006.01) |

(52) U.S. Cl.
CPC ............ *A61K 45/06* (2013.01); *A61K 9/0019* (2013.01); *A61K 31/05* (2013.01); *A61K 31/352* (2013.01); *A61K 31/7088* (2013.01); *A61K 31/713* (2013.01); *A61K 31/7105* (2013.01); *C12Q 1/6811* (2013.01); *C12Q 2525/207* (2013.01); *C12Q 2525/301* (2013.01)

(58) Field of Classification Search
CPC ............ C12Q 1/6811; C12Q 2525/207; C12Q 2525/301; A61K 31/05; A61K 31/7088; A61K 31/7105; A61K 31/713; A61K 45/06; A61K 9/0019; A61K 31/352

See application file for complete search history.

(56) References Cited

U.S. PATENT DOCUMENTS 9,789,172 B2 * 10/2017 Hadden .................... A61P 31/00
2015/0291964 A1 * 10/2015 Ichim .................. A61K 31/7105
                                                                           514/44 A

OTHER PUBLICATIONS

Massi, P. et al.; Cannabidiol as potential anticancer drug. Apr. 17, 2012, British Journal of Clinical Pharmacology. 75:2 303-312 (Year: 2012).*
Zuardi, A.; History of Cannabis as a Medicine: a Review. 2006 Brazilian Journal of Psychiatry 28:2 (Year: 2006).*
Smith, E.; High throughput screen for compounds to the orphan nuclear receptor NR2F6. 2022 SLAS Discovery. 27, 242-248 (Year: 2022).*

* cited by examiner

*Primary Examiner* — Mark L Shibuya
*Assistant Examiner* — Luisalberto Gonzalez
(74) *Attorney, Agent, or Firm* — Baumgartner Patent Law; Marc Baumgartner (57) ABSTRACT

Disclosed are means of stimulating systemic immunity and reduction of post-surgery tumor metastasis through the concurrent intralymphatic inhibition of NR2F6 and treatment with cannabidiol. In some embodiments NR2F6 is inhibited by high pressure transient delivery of short interfering RNA into tumor draining lymph nodes concurrent with systemic administration of cannabidiol. This combination may be performed together with means that induce immunogenic tumor cell death. Through the combination of immunogenic cell death and immune stimulation, the invention provides a means of enhancing the abscopal effect and in some embodiments to cause immunological mediated destruction primary and secondary neoplasia.

19 Claims, 1 Drawing Sheet

REDUCTION OF POST-SURGERY CANCER METASTASIS BY COMBINATION OF CANNABIDIOL AND NR2F6 INHIBITION

CROSS-REFERENCE TO RELATED APPLICATIONS

This application claims the benefit of priority to U.S. Provisional Application No. 62/885,740, filed Aug. 12, 2019, the contents of which are incorporated herein by reference.

BACKGROUND OF THE INVENTION

Treatment of cancer has historically been through surgery. Although no questions can be made about the appropriateness of debulking tumor masses, especially when they are impinging on vital organs or structures, there are some studies that show surgery may possess interesting, and sometimes pathological systemic effects. For example, one prevailing belief is that primary tumors secrete various anti-angiogenic compounds which suppress secondary micrometastatic tumors and that once primary tumors are removed, the lack of anti-angiogenic factors results in the metastatic tumors increasing in size (1-4).

It is known that cancer has been associated with inflammation since 1863, when Rudolf Virchow discovered leucocytes in neoplastic tissues and so made the first connection between inflammation and cancer. Since then, chronic inflammation has been deemed to be a risk factor for cancer. These reports demonstrate that an inflammatory environment supports tumour development and is consistent with that observed at tumour sites. However, the relationship of cancer with inflammation is not limited to the onset of the disease due to chronic inflammation. Schwartsburd proposed that chronic inflammation occurs due to tumour environment stress and that this generates a shield from the immune system. It has been recently demonstrated that the tumour microenvironment resembles an inflammation site, with significant support for tumour progression, through chemokines, cytokines, lymphocytes and macrophages which contribute to both the neovascularisation and vassal dilation for increased blood flow, the immunosuppression associated with the malignant disease, and the establishment of tumour metastasis. Furthermore, this inflammation-site tumour-generated microenvironment, apart from its significant role in protection from the immune system and promotion of cancer progression, has an adverse effect on the success of current cancer treatments. Indeed, it has been found that the inflammatory response in cancer can compromise the pharmacodynamics of chemotherapeutic agents.

Moreover, metastatic cancer cells leave the tumour as microcolonies, containing lymphocytes and platelets as well as tumour cells. Inflammation continues to play a role at metastatic sites by creating a cytokine milieu conducive to tumour growth. Immune homeostasis consists of a tightly regulated interplay of pro- and anti-inflammatory signals. For example, loss of the anti-inflammatory signals leads to chronic inflammation and proliferative signalling. Interestingly, cytokines that both promote and suppress proliferation of the tumour cells are produced at the tumour site. As in the case of cancer initiation, it is the imbalance between the effects of these various processes that results in tumour promotion.

SUMMARY

Embodiments herein include methods of inducing systemic immunity to a tumor comprising the steps of: a) selecting a patient suffering from a tumor; b) administering an inhibitor of NR2F6 intralymphatically; c) administering a cannabidiol; and d) inducing death of tumor tissue in an immunogenic manner.

According to certain embodiments said inhibitor of NR2F6 is a nucleic acid capable of inducing RNA interference.

According to certain embodiments said nucleic acid capable of inducing RNA interference is a short hairpin RNA.

According to certain embodiments said nucleic acid capable of inducing RNA interference is a short interfering RNA.

According to certain embodiments said nucleic acid capable of inducing RNA interference is a miRNA According to certain embodiments said inhibitor of NR2F6 is an antisense oligonucleotide.

According to certain embodiments said inhibitor of NR2F6 is combination of compounds capable of inducing gene editing.

According to certain embodiments said inhibitor of NR2F6 is a small molecule.

According to certain embodiments said intralymphatic administration may mean perilymphatic administration.

According to certain embodiments said perilymphatic administration is performed by a subcutaneous injection proximal to an area that drains into one or a plurality of lymph nodes.

According to certain embodiments said perilymphatic administration is performed by a intradermal injection proximal to an area that drains into one or a plurality of lymph nodes.

According to certain embodiments said area that drains into one or a plurality of lymph nodes is identified by manual means.

According to certain embodiments said area that drains into one or a plurality of lymph nodes is identified by a visualization means.

According to certain embodiments said visualization means is comprised of lymphangiography.

Certain embodiments are directed to methods of reducing post surgical tumor metastasis comprising the steps of: a) selecting a patient suffering from a tumor; b) administering an inhibitor of NR2F6 systemically; and c) administering a cannabidiol.

According to certain embodiments said inhibitor of NR2F6 is a nucleic acid capable of inducing RNA interference.

According to certain embodiments said nucleic acid capable of inducing RNA interference is a short hairpin RNA.

According to certain embodiments said nucleic acid capable of inducing RNA interference is a short interfering RNA.

According to certain embodiments said nucleic acid capable of inducing RNA interference is a miRNA According to certain embodiments said inhibitor of NR2F6 is an antisense oligonucleotide.

According to certain embodiments said inhibitor of NR2F6 is combination of compounds capable of inducing gene editing.

According to certain embodiments said inhibitor of NR2F6 is a small molecule.

According to certain embodiments intralymphatic administration means perilymphatic administration.

According to certain embodiments said perilymphatic administration is performed by a subcutaneous injection proximal to an area that drains into one or a plurality of lymph nodes.

According to certain embodiments said perilymphatic administration is performed by a intradermal injection proximal to an area that drains into one or a plurality of lymph nodes.

According to certain embodiments said area that drains into one or a plurality of lymph nodes is identified by manual means.

According to certain embodiments said area that drains into one or a plurality of lymph nodes is identified by a visualization means.

According to certain embodiments said visualization means is comprised of lymphangiography.

DESCRIPTION OF THE INVENTION

In one embodiment the invention teaches augmentation of chemotherapy efficacy by administration of intralymphatic inhibitors of NR2F6 combined with systemic administration of cannabidiol. Generally speaking, the concept of chemotherapy has been associated with blockade of cellular proliferation, either non-specific or semi-specific to cancer cells. Specifically, chemotherapy blocks DNA replication, which results in the death of cells in cell cycle. The molecular means by which chemotherapy acts on neoplastically transformed cells includes evocation of DNA damage, suppression of DNA copying and repair, and overall blocking the cells from dividing. The fact that chemotherapy kills all the cells that are cycling, results in killing of hematopoietic derived cells including cells of the immune system, which causes the typical immune suppression seen clinically in cancer patients. Furthermore, the immune suppressive effects of chemotherapy have been used clinically to combat autoimmune diseases.

Despite the dogma that chemotherapy is immune suppressive, recent studies have implicated an immunological component to various types of chemotherapy. For example, it is well known that cyclophosphamide, besides acting as an antimetabolite, has been shown to deplete T regulatory cells (5), and thus allowing it to be used as part of immunotherapy cocktails (6-9). Other types of chemotherapy also have been postulated to function, in part, through immunological means. For example, some types of chemotherapy induce a type of cell death called "immunogenic cell death."

The immune system sees cell death in two different ways. Apoptotic cell death, otherwise known as "programmed cell death" is a physiological process in which the intracellular materials are enclosed in apoptotic bodies and cleared by cells of the reticuloendothelial system, such as macrophages. During clearance of apoptotic cells, the membrane molecule of the apoptotic bodies, including phosphotidylserine, serve to induce an anti-inflammatory state, thus preventing initiation of immune responses to cells that die due to physiological need for their death. Examples include pruning of excess neurons in during brain development and death of senescent cells. In contrast, cell death induced by injury, results in a process called "necrosis" in which the internal contents of cells are released. This type of cell death causes activation of immune responses, due in part to the immunogenic nature of intracellular molecules such as histones, HMGB-1, and various heat shock proteins.

It is known that doxorubicin and oxaliplatin cause immunogenic cell death in cancer cells. In an elegant set of experiments, Krysco et al showed that doxorubicin caused sterile activation of innate immunity characterized by infiltration of neutrophils and macrophages. They showed that this inflammatory innate response was significantly reduced in mice deficient in myeloid differentiation primary response gene 88 (MyD88), TLR-2 or TLR-9. Stunningly, the investigators showed that chemical blockade of TLR-9 reduced the efficacy and the recruitment of neutrophils induced by doxorubicin (10). Using another model system, Inoue et al. compared cell death of the neuroblastoma cell line (neuro-2a cells) induced by doxorubicin or cisplatin, as well as CD8 T cell responses to dying cells in the presence of dendritic cells for induction of antigen presentation. It was found that CD8 cell multiplied more vigorously and produced high levels of interferon gamma in response to cancer cells dying from doxorubicin but not cisplatin. Furthermore, dendritic cell maturation was found to occur in the cells treated with doxorubicin but not cisplatin (11). Accordingly, the invention teaches, in some embodiments, the combination between intralymphatic administration of NR2F6 inhibitors together with systemic cannabidiol.

At a molecular level, immunogenic cell death in cancer cells has been defined by several features. The first is augmentation of cell surface expression of calreticulin, which is responsible for the phagocytosis of tumor cells undergoing immunogenic cell death by dendritic cells (DC). In what was termed discovery of "a good cell death for immunotherapy", the group of Guido Kroemer, found that anthracyclins induce the rapid, preapoptotic translocation of calreticulin (CRT) to the cell surface. Blockade or knockdown of CRT suppressed the phagocytosis of anthracyclin-treated tumor cells by dendritic cells and abolished their immunogenicity in mice. The anthracyclin-induced CRT translocation was mimicked by inhibition of the protein phosphatase 1/GADD34 complex. Administration of recombinant CRT or inhibitors of protein phosphatase 1/GADD34 restored the immunogenicity of cell death elicited by etoposide and mitomycin C, and enhanced their antitumor effects in vivo (12). In some animal models of cancer, there have been studies showing that deficiency of T cells, but not B cells, abrogates the anticancer effect of chemotherapy, thus supporting the importance of immune activities (13-15). Conversely, combinations of chemotherapy and immunotherapy have demonstrated synergy. In one study, melphalan, an alkylating agent commonly used to treat multiple myeloma, was investigated for activity on endogenous immune cells as well as adoptively transferred tumor-specific CD4(+) T cells in tumor-bearing mice. It was found that melphalan treatment resulted in a rapid burst of inflammatory cytokines and chemokines during the cellular recovery phase after melphalan-induced myelodepletion and leukodepletion. After melphalan treatment, tumor cells exhibited characteristics of immunogenic cell death, including membrane translocation of the endoplasmic reticulum-resident calreticulin and extracellular release of high-mobility group box 1. Additionally, there was enhanced tumor Ag uptake by dendritic cells in the tumor-draining lymph node. Consistent with these immunomodulatory effects, melphalan treatment of tumor-bearing mice led to the activation of the endogenous CD8(+) T cells and, more importantly, effectively drove the clonal expansion and effector differentiation of adoptively transferred tumor-specific CD4(+) T cells. Notably, the combination of melphalan and CD4(+) T celladoptive cell therapy was more efficacious than either treatment alone in prolonging the survival of mice with advanced B cell lymphomas or colorectal tumors (16).

Demonstration of the clinical relevance of CRT on cancer cells was suggested by experiments which assessed whether CRT exposure at the cell surface (ecto-CRT) occurs in human cancer in response to anthracyclines in vivo, focusing on acute myeloid leukemia (AML), which is currently treated with a combination of aracytine and anthracyclines. Most of the patients benefit from the induction chemotherapy but relapse within 1-12 months. Expression of ecto-CRT on malignant blasts before and after induction chemotherapy was assessed. The researchers observed that leukemic cells from some patients exhibited ecto-CRT regardless of chemotherapy and that this parameter was not modulated by in vivo chemotherapy. In line with biological relevance to immunogenicity, it was found that high levels of ecto-CRT on malignant myeloblasts positively correlated with the ability of autologous T cells to secrete interferon-γ on stimulation with blast-derived dendritic cell (17). In another study in liquid tumors, malignant blasts from AML patients were shown to express the "danger" signals CRT, HSP70, and HSP90 on their plasma membrane and high levels of surface-exposed CRT correlated with an increased proportion of natural killer cells and effector memory CD4$^+$ and CD8$^+$ T cells in the periphery. Moreover, CRT exposure on the plasma membrane of malignant blasts positively correlated with the frequency of circulating T cells specific for leukemia-associated antigens, indicating that ecto-CRT favors the initiation of anticancer immunity in patients with AML. Finally, although the levels of ecto-HSP70, ecto-HSP90, and ecto-CRT were all associated with improved relapse-free survival, only CRT exposure significantly correlated with superior overall survival (18). Similar findings were found in solid tumors, in one study, HMGB1 and CRT was evaluated by immunohistochemistry in pre-treatment biopsy specimens and surgically resected specimens, which were obtained from patients with breast cancer (n=52) and esophageal squamous cell carcinoma (ESCC) (n=8) who had been treated with neoadjuvant chemotherapy (NAC). HMGB1 and calreticulin expression was analyzed in breast cancer cell lines treated with chemotherapeutic drugs. As a result, both HMGB1 and calreticulin expression levels were significantly upregulated after NAC in both breast cancer and ESCC tissues. Overall survival in the high infiltration group of CD8-positive T cells was significantly superior to that in the low infiltration group in breast cancer patients, there were positive correlations between the number of CD8-positive T cells and HMGB1 and CRT (19).

The invention teaches means of activating abscopal effect in cancer patients and enhancing such systemic effects through induction of RNA interference in order to silence or significantly inhibit expression of NR2F6, while substantially administering cannabidiol at a concentration to inhibit chronic inflammation.

The use of cannabidiol to inhibit chronic inflammation has been shown by others but never in this context. We provide other examples of utilizing cannabidiol to inhibit chronic inflammation to each one of skill in the art to utilize cannabidiol. In one study, vitro effects of both psychoactive and nonpsychoactive marijuana components on leukocyte secretion of the immunoregulatory cytokines interleukin-1 alpha (IL-1), tumor necrosis factor alpha (TNF), interferon-gamma (IFN) and interleukin-2 (IL-2) where investigated. The psychoactive delta-9-tetrahydrocannabinol (THC) and nonpsychoactive cannabidiol (CBD) were added to cultures of mitogen-activated human peripheral blood mononuclear cells (PBMC) and the concentrations of IL-1, TNF, IFN and IL-2 in culture supernatants were measured by ELISA systems. Concentrations of THC and CBD, comparable to plasma levels found after smoking marijuana (10-100 ng/ml), increased the concentration of measurable IFN (139 and 68%), while high concentrations of both cannabinoids (5-20 micrograms/ml) completely blocked synthesis and/or release of this cytokine. CBD was also shown to decrease the measurable quantity of both IL-1 and TNF. In contrast to the effects on IFN, IL-1 and TNF, both cannabinoids, had no effect on IL-2 secretion (20). It is known that type 1 diabetes is associated with inflammatory response activation in the pancreas as a result of autoimmune attack, causing loss of insulin production. In one study it as shown that cannabidiol (CBD) treatment significantly reduces the incidence of diabetes in NOD mice from an incidence of 86% in non-treated control mice to an incidence of 30% in CBD-treated mice. CBD treatment also resulted in the significant reduction of plasma levels of the pro-inflammatory cytokines, IFN-gamma and TNF-alpha. Th1-associated cytokine production of in vitro activated T-cells and peritoneal macrophages was also significantly reduced in CBD-treated mice, whereas production of the Th2-associated cytokines, IL-4 and IL-10, was increased when compared to untreated control mice. Histological examination of the pancreatic islets of CBD-treated mice revealed significantly reduced insulitis. These data indicate that CBD can inhibit and delay destructive insulitis and inflammatory Th1-associated cytokine production in NOD mice resulting in a decreased incidence of diabetes possibly through an immunomodulatory mechanism shifting the immune response from Th1 to Th2 dominance (21).

In some embodiments the invention teaches to amplify the abscopal effect by treatment with cannabidiol and NR2F6 inhibition. In some embodiments, the abscopal effect is induced by irradiation in a manner to cause localized tumor cell death. One of the first described examples of abscopal effect was published in 1975 when systemic melanoma metastasis started regressing after localized radiation treatment (22). Ohba et al reported the case of a 76 year old Japanese man with hepatocellular carcinoma that regressed after radiotherapy for thoracic vertebral bone metastasis. Serum levels of tumour necrosis factor-alpha increased after radiotherapy. The findings suggests that such abscopal related regression may be associated with host immune response, involving cytokines such as tumour necrosis factor-alpha (23). Another case was reported of a 69-year-old woman with advanced uterine cervical carcinoma with toruliform para-aortic lymph node metastases that showed an abscopal effect of radiation therapy (effect out of irradiated field). The patient was admitted to hospital in March 2005, and treated with radiation therapy only for the primary pelvic lesions without chemotherapy because of her severe economic status. After the treatment, not only did the cervical tumor in the irradiated field disappear, but the toruliform para-aortic lymph node swelling outside the irradiated field also spontaneously disappeared. The patient is still alive and well without relapse (24). Okuma et al reported on a 63-year-old Japanese man underwent extended right hepatic lobectomy for hepatocellular carcinoma. During his follow-up examination, a single lung metastasis and a single mediastinal lymph node metastasis were found. Trans-catheter arterial embolization was initially attempted to treat the mediastinal tumor, however this approach failed to take effect and carried risks of spinal artery embolism. External-beam irradiation, with a dose of 2.25 Gy per fraction, was performed using an anterior-posterior parallel-opposed technique (total dose, 60.75 Gy). A computed tomography scan performed one month after starting radiotherapy showed a remarkable reduction of the mediastinal lymph node metastasis. In addition to this, they observed spontaneous shrinking of the lung metastasis, which was located in the right lower lobe and out of the radiation field. No chemotherapy was given during the period. There has been no recurrence of either the lung metastasis or the mediastinal lymph node metastasis during a follow-up 10 years after the radiotherapy (25). In another report an 80-year-old male with squamous cell carcinoma with bilobar hepatic metastases who underwent targeted Yttrium-90 radioembolization of the right hepatic lobe lesion. Subsequently, there was complete regression of the nontargeted, left hepatic lobe lesion (26).

Cases of abscopal effect have also been observed in chronic lymphocytic leukemia (27,28), Merkel Cell Carcinoma (29), melanoma (30-32), renal cell carcinoma (33), myeloma (34), pancreatic cancer (35,36), breast cancer (37,38), renal cell carcinoma (39), diffuse Giant tumor (40), and non-small cell lung cancer (41).

In some embodiments, administration of cannabidiol is performed to repair microbiome dysbiosis. Various antibiotics, by ability to suppress the gut microbiota, have been shown to inhibit immune function. For example, Leiva et al showed that treatment with non-absorbable antibiotics polymyxin B or teicoplanin by the intragastric route led to suppression of spleen cells to proliferate in response to B-cell and T-cell mitogens (42).

In another study, the role of the microbiota in anticancer immunity was assessed. It was found that antibiotic-treated (Abt) mice were more susceptible to development of engrafted B16/F10 melanoma and Lewis lung carcinoma, exhibiting a shortened mean survival time with more numerous and larger tumor foci in the lungs. Importantly, the study demonstrated that the defective antitumor response of Abt mice was independent of dehydration caused by antibiotics. Host defenses relied upon intact commensal bacteria with no class specificity. Mechanistic investigations revealed a defective induction of the γδT17 cell response in lungs of Abt mice; here, more aggressive tumor development was observed, possibly related to a reduction in IL6 and IL23 expression there. Adding normal γδT cells or supplementing IL17 restored the impaired immune surveillance phenotype in Abt mice (43). In another oncology study, mice with lewis lung carcinoma were treated with cisplatin combined with ABX (an antibiotic cocktail of vancomycin, ampicillin, and neomycin), which can destroy the host commensal microflora, the tumor size was larger than in mice on a single treatment of cisplatin. Moreover, the survival rate of mice treated with cisplatin combined with ABX was significantly reduced. In contrast, mice treated with cisplatin combined with Lactobacillus bacteria had smaller tumors and an improved survival rate. Further study on gene expression indicated that ABX can partially impair the function of cisplatin by upregulating the expression of VEGFA and downregulating the expression of BAX and CDKN1B. The expression of IFN-γ, GZMB, and PRF1 in the CD8(+) T cells of these mice was reduced by ABX, indicating the importance of gut microbiota to an intact immune system. On the other hand, Lactobacillus co-treatment mice showed an enhanced antitumor response with upregulated IFN-γ, GZMB, and PRF1 expression (44).

One of the most important demonstrations of the fundamental role the host microbiome plays in cancer immunity was from Laurence Zitvogel's group in which they found that primary resistance to immune checkpoint inhibitors can be attributed to the state of gut microbiome composition. Specifically, the researchers showed that antibiotics inhibited the clinical benefit of immune checkpoint inhibitors in patients with advanced cancer. Fecal microbiota transplantation (FMT) from cancer patients who responded to immune checkpoint inhibitors into germ-free or antibiotic-treated mice ameliorated the antitumor effects of PD-1 blockade, whereas FMT from nonresponding patients failed to do so. Metagenomics of patient stool samples at diagnosis revealed correlations between clinical responses to immune checkpoint inhibitors and the relative abundance of *Akkermansia muciniphila* Oral supplementation with *A. muciniphila* after FMT with nonresponder feces restored the efficacy of PD-1 blockade in an interleukin-12-dependent manner by increasing the recruitment of $CCR9^+CXCR3^+$ $CD4^+$ T lymphocytes into mouse tumor beds (45).

Weakening of immune responses as a result of gut microbiome ablation has been described in models outside of oncology, such as in development of antiviral immunity (46,47), anti-parasitic immunity (48), protection of T cells from apoptosis (49,50), recall responses to vaccination (51, 52), macrophage activation (53). In one study long-term intermittent fasting (IF) was shown to protect against diabetic retinopathy (DR) in mice by restructuring the microbiome. Microbiome analysis revealed IF induced increased levels of Firmicutes and decreased Bacteroidetes and Verrucomicrobia in the gut. Consistent with the known modulatory effects of Firmicutes on bile acid (BA) metabolism, measurement of BAs demonstrated a significant increase of tauroursodeoxycholate (TUDCA), a neuroprotective BA, in db/db on IF but not in db/db on regular feeding. TGR5, the TUDCA receptor, was found in the retinal primary ganglion cells. Expression of TGR5 did not change with IF or diabetes. However, IF reduced retinal TNF-α mRNA, which is a downstream target of TGR5 activation These findings support the concept that IF prevents DR by restructuring the microbiota toward species producing TUDCA and subsequent retinal protection by TGR5 activation (54). In some embodiments the addition of fasting to a treatment regimen is utilized to enhance anticancer activity. Another study demonstrated that weigh loss in mice associated with intermittent fasting was dependent on alterations of the microbiome. The investigators showed that an every-other-day fasting (EODF) regimen selectively stimulated beige fat development within white adipose tissue and dramatically ameliorates obesity, insulin resistance, and hepatic steatosis. EODF treatment results in a shift in the gut microbiota composition leading to elevation of the fermentation products acetate and lactate and to the selective upregulation of monocarboxylate transporter 1 expression in beige cells. Microbiota-depleted mice were resistance to EODF-induced beiging, while transplantation of the microbiota from EODF-treated mice to microbiota-depleted mice activates beiging and improves metabolic homeostasis. These findings provide a new gut-microbiota-driven mechanism for activating adipose tissue browning and treating metabolic diseases (55).

Another study demonstrated that the inhibition of autoimmune inflammation in an animal model of multiple sclerosis by IF is mediated through modulation of the gut microbiome. It was shown that IF ameliorated clinical course and pathology of the MS model, experimental autoimmune encephalomyelitis (EAE). IF led to increased gut bacteria richness, enrichment of the Lactobacillaceae, Bacteroidaceae, and Prevotellaceae families and enhanced antioxidative microbial metabolic pathways. IF altered T cells in the gut with a reduction of IL-17 producing T cells and an increase in regulatory T cells. Fecal microbiome transplantation from mice on IF ameliorated EAE in immunized recipient mice on a normal diet, suggesting that IF effects are at least partially mediated by the gut flora. In a pilot clinical trial in MS patients, intermittent energy restriction altered blood adipokines and the gut flora resembling protective changes observed in mice. In conclusion, IF has potent immunomodulatory effects that are at least partially mediated by the gut microbiome (56).

In one experiment obese ob/ob mice were subjected to a normal, low-capsaicin (0.01%), or high-capsaicin (0.02%) diet for 6 weeks, respectively. Obesity phenotypes, glucose homeostasis, the gut microbiota structure and composition, short-chain fatty acids, gastrointestinal hormones, and pro-inflammatory cytokines were measured. Dietary capsaicin at both the low and high doses significantly inhibited the increase of fasting blood glucose and insulin levels. These inhibitory effects were comparable between the two groups. Similarly, dietary capsaicin resulted in remarkable improvement in glucose and insulin tolerance. In addition, neither the low- nor high-capsaicin diet could alter the α-diversity and β-diversity of the gut microbiota. Taxonomy-based analysis showed that both the low- and high-capsaicin diets, acting in similar ways, significantly increased the Firmicutes/Bacteroidetes ratio at the phylum level as well as increased the *Roseburia* abundance and decreased the *Bacteroides* and *Parabacteroides* abundances at the genus level. Spearman's correlation analysis revealed that the *Roseburia* abundance was negatively while the *Bacteroides* and *Parabacteroides* abundances were positively correlated to the fasting blood glucose level and area under the curve by the oral glucose tolerance test. Finally, the low- and high-capsaicin diets significantly increased the fecal butyrate and plasma total GLP-1 levels, but decreased plasma total ghrelin, TNF-α, IL-β, and IL-6 levels as compared with the normal diet. These studies suggest that beneficial effects of dietary capsaicin on glucose homeostasis are likely associated with the alterations of specific bacteria at the genus level. These alterations in bacteria induced by dietary capsaicin contribute to improved glucose homeostasis through increasing short-chain fatty acids, regulating gastrointestinal hormones and inhibiting pro-inflammatory cytokines (57).

Cinnamon bark (CBE) and grape pomace (GPE) are known to be associated with weight loss, and a recent study suggested that this may be occurring via modulation of the microbiome. The study used C57BL/6J mice fed a high-fat diet (HFD) for 8 weeks. Both CBE and GPE were able to decrease fat mass gain and adipose tissue inflammation in mice fed a HFD without reducing food intake. The amelioration of the overall metabolic profile were associated to a significant impact on the microbial composition, which was more profound for the GPE than for the CBE. At the genus level, Peptococcus were decreased in the CBE group. In the GPE treated group, several key genera that have been previously found to be linked with HFD, metabolic effects and gut barrier integrity were affected: we observed a decrease of Desulfovibrio, Lactococcus, whereas Allobaculum and Roseburia were increased. In addition, the expression of several antimicrobial peptides and tight junction proteins was increased in response to both CBE and GPE supplementation, indicating an improvement of the gut barrier function. Collectively, these data suggest that CBE and GPE can ameliorate the overall metabolic profile of mice on a high-fat diet, partly by acting on the gut microbiota (58).

Alteration of diet in humans also induces beneficial effects by modification of the microbiome. For example, in one study, 268 non-diabetic individuals were stratified into groups of dietary types (strict vegetarians, lacto-ovo-vegetarians, and omnivores). The taxonomic composition and phylogenetic structure of the microbiota were obtained through the analysis of the 16S rRNA gene. The sample (54.2% women, mean age 49.5 years) was composed of 66 strict vegetarians, 102 lacto-ovo-vegetarians and 100 omnivores. Considering the entire sample, the greatest abundant phyla were Firmicutes (40.7±15.9%) and Bacteroidetes (39.5±19.9%), and no difference in abundances was found between individuals with normal and excess weight. Stratifying by dietary types, the proportion of Firmicutes was lower and of Bacteroidetes was higher in strict vegetarians when compared to lacto-ovo-vegetarians and omnivores. At the genus level, strict vegetarians had a higher *Prevotella* abundance and *Prevotella/Bacteroides* ratio than the other groups. They also had a lower proportion of *Faecalibacterium* than lacto-ovo-vegetarians, and both vegetarian groups had higher proportions than did omnivores. *Succinivibrio* and *Halomonas* from the Proteobacteria phylum were over-represented in omnivores. The omnivorous group showed higher values of anthropometric data, insulin, HOMA-IR, and a worse lipid profile Inflammatory markers exhibited a gradual and significant increase from the vegetarians and lacto-ovo-vegetarians to the omnivorous group. Based on the findings relative to bacteria abundances and on their recognized actions in the metabolism, the authors suggested that exposure to animal foods may favor an intestinal environment which could trigger systemic inflammation and insulin resistance-dependent metabolic disorders (59).

In some embodiments T cells are administered intralymphatically, wherein said T cells may be previously activated ex vivo. T cells may be conditioned before administration by exposure to hypoxia. In one embodiment this may be performed by exposure of T cells to hypoxic conditions, specifically hypoxic conditions can comprise an oxygen level of lower than 10%. In some embodiments, hypoxic conditions comprise up to about 7% oxygen. For example, hypoxic conditions can comprise up to about 7%, up to about 6%, up to about 5%, up to about 4%, up to about 3%, up to about 2%, or up to about 1% oxygen. As another example, hypoxic conditions can comprise up to 7%, up to 6%, up to 5%, up to 4%, up to 3%, up to 2%, or up to 1% oxygen. In some embodiments, hypoxic conditions comprise about 1% oxygen up to about 7% oxygen. For example, hypoxic conditions can comprise about 1% oxygen up to about 7% oxygen; about 2% oxygen up to about 7% oxygen; about 3% oxygen up to about 7% oxygen; about 4% oxygen up to about 7% oxygen; about 5% oxygen up to about 7% oxygen; or about 6% oxygen up to about 7% oxygen. As another example, hypoxic conditions can comprise 1% oxygen up to 7% oxygen; 2% oxygen up to 7% oxygen; 3% oxygen up to 7% oxygen; 4% oxygen up to 7% oxygen; 5% oxygen up to 7% oxygen; or 6% oxygen up to 7% oxygen. As another example, hypoxic conditions can comprise about 1% oxygen up to about 7% oxygen; about 1% oxygen up to about 6% oxygen; about 1% oxygen up to about 5% oxygen; about 1% oxygen up to about 4% oxygen; about 1% oxygen up to about 3% oxygen; or about 1% oxygen up to about 2% oxygen. As another example, hypoxic conditions can comprise 1% oxygen up to 7% oxygen; 1% oxygen up to 6% oxygen; 1% oxygen up to 5% oxygen; 1% oxygen up to 4% oxygen; 1% oxygen up to 3% oxygen; or 1% oxygen up to 2% oxygen. As another example, hypoxic conditions can comprise about 1% oxygen up to about 7% oxygen; about 2% oxygen up to about 6% oxygen; or about 3% oxygen up to about 5% oxygen. As another example, hypoxic conditions can comprise 1% oxygen up to 7% oxygen; 2% oxygen up to 6% oxygen; or 3% oxygen up to 5% oxygen. In some embodiments, hypoxic conditions can comprise no more than about 2% oxygen. For example, hypoxic conditions can comprise no more than 2% oxygen.

Example: Suppression of Lung Metastasis after Resection of 4T1 Breast Cancer Cells Breast cancer 4T1 cells were maintained in RPMI-1640 supplemented with 10% FBS, 100 µM non-essential amino acids, 100 µM sodium pyruvate, 100 m/ml streptomycin and 100 unit/ml penicillin. Cells where cultured in a standard 5% $CO_2$ incubator at 37° C. In order to induce metastasis, mice were injected subcutaneously with 4T1 cells ($5 \times 10^5$ cells/50 µl PBS/mouse) into the fourth mammary fat pad under isoflurane anesthesia. Tumor growth was monitored by measuring the tumor volume, as length×(width)$^2$/2. After tumors were established (180-200 mm$^3$) on day 15, test mice were divided into groups (8 mice/group) and subjected to different treatments. At 16 days post tumor cell implantation, primary tumors were surgically resected and incisions closed with sutures.

Mice were treated with cannabidiol, short interfering RNA targeting NR2F6, and the combination.

Figure 1:
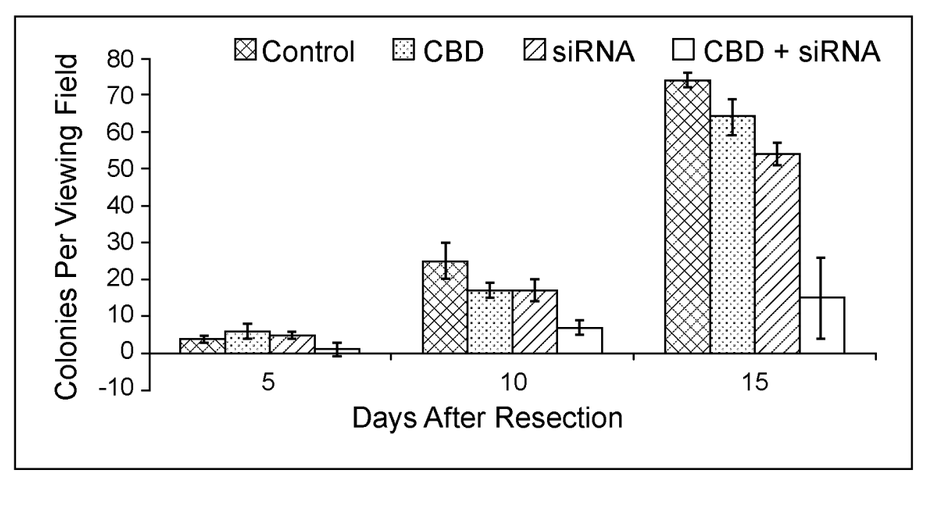
The FIGURE is a bar graph showing the results of tumorous mice being treated with cannabidiol, short interfering RNA targeting NR2F6, and the combination. As shown, mice treated with the combination resulted in the lowest number of tumor colonies.

Mice were sacrificed at 5, 10 and 15 days after resection and the number of metastatic colonies was counted microscopically. Results are shown in the graph of the FIGURE.

REFERENCES

1. Hanin, L., and Rose, J. (2018) Suppression of Metastasis by Primary Tumor and Acceleration of Metastasis Following Primary Tumor Resection: A Natural Law? *Bull Math Biol* 80, 519-539
2. Hanin, L., and Bunimovich-Mendrazitsky, S. (2014) Reconstruction of the natural history of metastatic cancer and assessment of the effects of surgery: Gompertzian growth of the primary tumor. *Math Biosci* 247, 47-58
3. Naumov, G. N., Folkman, J., Straume, O., and Akslen, L. A. (2008) Tumor-vascular interactions and tumor dormancy. *APMIS* 116, 569-585
4. Hanin, L., and Korosteleva, O. (2010) Does extirpation of the primary breast tumor give boost to growth of metastases? Evidence revealed by mathematical modeling. *Math Biosci* 223, 133-141
5. Noordam, L., Kaijen, M. E. H., Bezemer, K., Cornelissen, R., Maat, L., Hoogsteden, H. C., Aerts, J., Hendriks, R. W., Hegmans, J., and Vroman, H. (2018) Low-dose cyclophosphamide depletes circulating naive and activated regulatory T cells in malignant pleural mesothelioma patients synergistically treated with dendritic cell-based immunotherapy. *Oncoimmunology* 7, e1474318
6. Wu, J., and Waxman, D. J. (2015) Metronomic cyclophosphamide eradicates large implanted GL261 gliomas by activating antitumor Cd8(+) T-cell responses and immune memory. *Oncoimmunology* 4, e1005521
7. Keenan, B. P., Saenger, Y., Kafrouni, M. I., Leubner, A., Lauer, P., Maitra, A., Rucki, A. A., Gunderson, A. J., Coussens, L. M., Brockstedt, D. G., Dubensky, T. W., Jr., Hassan, R., Armstrong, T. D., and Jaffee, E. M. (2014) A Listeria vaccine and depletion of T-regulatory cells activate immunity against early stage pancreatic intraepithelial neoplasms and prolong survival of mice. *Gastroenterology* 146, 1784-1794 e1786
8. Tongu, M., Harashima, N., Monma, H., Inao, T., Yamada, T., Kawauchi, H., and Harada, M. (2013) Metronomic chemotherapy with low-dose cyclophosphamide plus gemcitabine can induce anti-tumor T cell immunity in vivo. *Cancer Immunol Immunother* 62, 383-391
9. Betting, D. J., Hurvitz, S. A., Steward, K. K., Yamada, R. E., Kafi, K., van Rooijen, N., and Timmerman, J. M. (2012) Combination of cyclophosphamide, rituximab, and intratumoral CpG oligodeoxynucleotide successfully eradicates established B cell lymphoma. *J Immunother* 35, 534-543
10. Krysko, D. V., Kaczmarek, A., Krysko, O., Heyndrickx, L., Woznicki, J., Bogaert, P., Cauwels, A., Takahashi, N., Magez, S., Bachert, C., and Vandenabeele, P. (2011) TLR-2 and TLR-9 are sensors of apoptosis in a mouse model of doxorubicin-induced acute inflammation. *Cell Death Differ* 18, 1316-1325
11. Inoue, S., Setoyama, Y., and Odaka, A. (2014) Doxorubicin treatment induces tumor cell death followed by immunomodulation in a murine neuroblastoma model. *Exp Ther Med* 7, 703-708
12. Obeid, M., Tesniere, A., Ghiringhelli, F., Fimia, G. M., Apetoh, L., Perfettini, J. L., Castedo, M., Mignot, G., Panaretakis, T., Casares, N., Metivier, D., Larochette, N., van Endert, P., Ciccosanti, F., Piacentini, M., Zitvogel, L., and Kroemer, G. (2007) Calreticulin exposure dictates the immunogenicity of cancer cell death. *Nat Med* 13, 54-61
13. Aranda, F., Bloy, N., Pesquet, J., Petit, B., Chaba, K., Sauvat, A., Kepp, O., Khadra, N., Enot, D., Pfirschke, C., Pittet, M., Zitvogel, L., Kroemer, G., and Senovilla, L. (2015) Immune-dependent antineoplastic effects of cisplatin plus pyridoxine in non-small-cell lung cancer. *Oncogene* 34, 3053-3062
14. Aranda, F., Bloy, N., Galluzzi, L., Kroemer, G., and Senovilla, L. (2014) Vitamin B6 improves the immunogenicity of cisplatin-induced cell death. *Oncoimmunology* 3, e955685
15. Hannani, D., Locher, C., Yamazaki, T., Colin-Minard, V., Vetizou, M., Aymeric, L., Viaud, S., Sanchez, D., Smyth, M. J., Bruhns, P., Kroemer, G., and Zitvogel, L. (2014) Contribution of humoral immune responses to the antitumor effects mediated by anthracyclines. *Cell Death Differ* 21, 50-58
16. Lu, X., Ding, Z. C., Cao, Y., Liu, C., Habtetsion, T., Yu, M., Lemos, H., Salman, H., Xu, H., Mellor, A. L., and Zhou, G. (2015) Alkylating agent melphalan augments the efficacy of adoptive immunotherapy using tumor-specific CD4+ T cells. *J Immunol* 194, 2011-2021
17. Wemeau, M., Kepp, O., Tesniere, A., Panaretakis, T., Flament, C., De Botton, S., Zitvogel, L., Kroemer, G., and Chaput, N. (2010) Calreticulin exposure on malignant blasts predicts a cellular anticancer immune response in patients with acute myeloid leukemia. *Cell Death Dis* 1, e104
18. Fucikova, J., Truxova, I., Hensler, M., Becht, E., Kasikova, L., Moserova, I., Vosahlikova, S., Klouckova, J., Church, S. E., Cremer, I., Kepp, O., Kroemer, G., Galluzzi, L., Salek, C., and Spisek, R. (2016) Calreticulin exposure by malignant blasts correlates with robust anti-cancer immunity and improved clinical outcome in AML patients. *Blood* 128, 3113-3124
19. Aoto, K., Mimura, K., Okayama, H., Saito, M., Chida, S., Noda, M., Nakajima, T., Saito, K., Abe, N., Ohki, S., Ohtake, T., Takenoshita, S., and Kono, K. (2018) Immunogenic tumor cell death induced by chemotherapy in patients with breast cancer and esophageal squamous cell carcinoma. *Oncol Rep* 39, 151-159

20. Watzl, B., Scuderi, P., and Watson, R. R. (1991) Marijuana components stimulate human peripheral blood mononuclear cell secretion of interferon-gamma and suppress interleukin-1 alpha in vitro. *Int J Immunopharmacol* 13, 1091-1097

21. Weiss, L., Zeira, M., Reich, S., Har-Noy, M., Mechoulam, R., Slavin, S., and Gallily, R. (2006) Cannabidiol lowers incidence of diabetes in non-obese diabetic mice. *Autoimmunity* 39, 143-151

22. Kingsley, D. P. (1975) An interesting case of possible abscopal effect in malignant melanoma. *Br J Radiol* 48, 863-866

23. Ohba, K., Omagari, K., Nakamura, T., Ikuno, N., Saeki, S., Matsuo, I., Kinoshita, H., Masuda, J., Hazama, H., Sakamoto, I., and Kohno, S. (1998) Abscopal regression of hepatocellular carcinoma after radiotherapy for bone metastasis. *Gut* 43, 575-577

24. Takaya, M., Niibe, Y., Tsunoda, S., Jobo, T., Imai, M., Kotani, S., Unno, N., and Hayakawa, K. (2007) Abscopal effect of radiation on toruliform para-aortic lymph node metastases of advanced uterine cervical carcinoma—a case report. *Anticancer Res* 27, 499-503

25. Okuma, K., Yamashita, H., Niibe, Y., Hayakawa, K., and Nakagawa, K. (2011) Abscopal effect of radiation on lung metastases of hepatocellular carcinoma: a case report. *J Med Case Rep* 5, 111

26. Ghodadra, A., Bhatt, S., Camacho, J. C., and Kim, H. S. (2016) Abscopal Effects and Yttrium-90 Radioembolization. *Cardiovasc Intervent Radiol* 39, 1076-1080

27. Lakshmanagowda, P. B., Viswanath, L., Thimmaiah, N., Dasappa, L., Supe, S. S., and Kallur, P. (2009) Abscopal effect in a patient with chronic lymphocytic leukemia during radiation therapy: a case report. *Cases J* 2, 204

28. Aalbers, A. M., Aarts, M. J., Krol, A. D., Marijnen, C. A., and Posthuma, E. F. (2016) The beneficial local and abscopal effect of splenic irradiation in frail patients with chronic lymphocytic leukaemia. *Neth J Med* 74, 122-129

29. Cotter, S. E., Dunn, G. P., Collins, K. M., Sahni, D., Zukotynski, K. A., Hansen, J. L., O'Farrell, D. A., Ng, A. K., Devlin, P. M., and Wang, L. C. (2011) Abscopal effect in a patient with metastatic Merkel cell carcinoma following radiation therapy: potential role of induced antitumor immunity. *Arch Dermatol* 147, 870-872

30. Postow, M. A., Callahan, M. K., Barker, C. A., Yamada, Y., Yuan, J., Kitano, S., Mu, Z., Rasalan, T., Adamow, M., Ritter, E., Sedrak, C., Jungbluth, A. A., Chua, R., Yang, A. S., Roman, R. A., Rosner, S., Benson, B., Allison, J. P., Lesokhin, A. M., Gnjatic, S., and Wolchok, J. D. (2012) Immunologic correlates of the abscopal effect in a patient with melanoma. *N Engl J Med* 366, 925-931

31. Stamell, E. F., Wolchok, J. D., Gnjatic, S., Lee, N. Y., and Brownell, I. (2013) The abscopal effect associated with a systemic anti-melanoma immune response. *Int J Radiat Oncol Biol Phys* 85, 293-295

32. Grimaldi, A. M., Simeone, E., Giannarelli, D., Muto, P., Falivene, S., Borzillo, V., Giugliano, F. M., Sandomenico, F., Petrillo, A., Curvietto, M., Esposito, A., Paone, M., Palla, M., Palmieri, G., Caraco, C., Ciliberto, G., Mozzillo, N., and Ascierto, P. A. (2014) Abscopal effects of radiotherapy on advanced melanoma patients who progressed after ipilimumab immunotherapy. *Oncoimmunology* 3, e28780

33. Ishiyama, H., Teh, B. S., Ren, H., Chiang, S., Tann, A., Blanco, A. I., Paulino, A. C., and Amato, R. (2012) Spontaneous regression of thoracic metastases while progression of brain metastases after stereotactic radiosurgery and stereotactic body radiotherapy for metastatic renal cell carcinoma: abscopal effect prevented by the blood-brain barrier? *Clin Genitourin Cancer* 10, 196-198

34. Saba, R., Saleem, N., and Peace, D. (2016) Long-term survival consequent on the abscopal effect in a patient with multiple myeloma. *BMJ Case Rep* 2016

35. Ungaro, A., Orsi, F., Casadio, C., Galdy, S., Spada, F., Cella, C. A., Tonno, C. D., Bonomo, G., Vigna, P. D., Murgioni, S., Frezza, A. M., and Fazio, N. (2016) Successful palliative approach with high-intensity focused ultrasound in a patient with metastatic anaplastic pancreatic carcinoma: a case report. *Ecancermedicalscience* 10, 635

36. Shi, F., Wang, X., Teng, F., Kong, L., and Yu, J. (2017) Abscopal effect of metastatic pancreatic cancer after local radiotherapy and granulocyte-macrophage colony-stimulating factor therapy. *Cancer Biol Ther* 18, 137-141

37. Demaria, S., Vanpouille-Box, C., Formenti, S. C., and Adams, S. (2013) The TLR7 agonist imiquimod as an adjuvant for radiotherapy-elicited in situ vaccination against breast cancer. *Oncoimmunology* 2, e25997

38. Leung, H. W., Wang, S. Y., Jin-Jhih, H., and Chan, A. L. (2018) Abscopal effect of radiation on bone metastases of breast cancer: A case report. *Cancer Biol Ther* 19, 20-24

39. Van de Walle, M., Demol, J., Staelens, L., and Rottey, S. (2017) Abscopal effect in metastatic renal cell carcinoma. *Acta Clin Belg* 72, 245-249

40. Desar, I. M., Braam, P. M., Kaal, S. E., Gerritsen, W. R., Oyen, W. J., and van der Graaf, W. T. (2016) Abscopal effect of radiotherapy in a patient with metastatic diffuse-type giant cell tumor. *Acta Oncol* 55, 1510-1512

41. Cong, Y., Shen, G., Wu, S., and Hao, R. (2017) Abscopal regression following SABR for non-small-cell-lung cancer: A case report. *Cancer Biol Ther* 18, 1-3

42. Leiva, M., Moreno, E., Ruiz-Bravo, A., and Jimenez-Valera, M. (2005) Immunomodulation by non-absorbable antibiotics given by the intragastric route. *Int J Antimicrob Agents* 25, 252-255

43. Cheng, M., Qian, L., Shen, G., Bian, G., Xu, T., Xu, W., Shen, G., and Hu, S. (2014) Microbiota modulate tumoral immune surveillance in lung through a gammadeltaT17 immune cell-dependent mechanism. *Cancer Res* 74, 4030-4041

44. Gui, Q. F., Lu, H. F., Zhang, C. X., Xu, Z. R., and Yang, Y. H. (2015) Well-balanced commensal microbiota contributes to anti-cancer response in a lung cancer mouse model. *Genet Mol Res* 14, 5642-5651

45. Routy, B., Le Chatelier, E., Derosa, L., Duong, C. P. M., Alou, M. T., Daillere, R., Fluckiger, A., Messaoudene, M., Rauber, C., Roberti, M. P., Fidelle, M., Flament, C., Poirier-Colame, V., Opolon, P., Klein, C., Iribarren, K., Mondragon, L., Jacquelot, N., Qu, B., Ferrere, G., Clemenson, C., Mezquita, L., Masip, J. R., Naltet, C., Brosseau, S., Kaderbhai, C., Richard, C., Rizvi, H., Levenez, F., Galleron, N., Quinquis, B., Pons, N., Ryffel, B., Minard-Colin, V., Gonin, P., Soria, J. C., Deutsch, E., Loriot, Y., Ghiringhelli, F., Zalcman, G., Goldwasser, F., Escudier, B., Hellmann, M. D., Eggermont, A., Raoult, D., Albiges, L., Kroemer, G., and Zitvogel, L. (2018) Gut microbiome influences efficacy of PD-1-based immunotherapy against epithelial tumors. *Science* 359, 91-97

46. Gonzalez-Perez, G., Hicks, A. L., Tekieli, T. M., Radens, C. M., Williams, B. L., and Lamouse-Smith, E. S. (2016) Maternal Antibiotic Treatment Impacts Development of the Neonatal Intestinal Microbiome and Antiviral Immunity. *J Immunol* 196, 3768-3779
47. Ichinohe, T., Pang, I. K., Kumamoto, Y., Peaper, D. R., Ho, J. H., Murray, T. S., and Iwasaki, A. (2011) Microbiota regulates immune defense against respiratory tract influenza A virus infection. *Proc Natl Acad Sci USA* 108, 5354-5359
48. Keselman, A., Li, E., Maloney, J., and Singer, S. M. (2016) The Microbiota Contributes to CD8+ T Cell Activation and Nutrient Malabsorption following Intestinal Infection with Giardia duodenalis. *Infect Immun* 84, 2853-2860
49. Soto, R., Petersen, C., Novis, C. L., Kubinak, J. L., Bell, R., Stephens, W. Z., Lane, T. E., Fujinami, R. S., Bosque, A., O'Connell, R. M., and Round, J. L. (2017) Microbiota promotes systemic T-cell survival through suppression of an apoptotic factor. *Proc Natl Acad Sci USA* 114, 5497-5502
50. Ekmekciu, I., von Klitzing, E., Neumann, C., Bacher, P., Scheffold, A., Bereswill, S., and Heimesaat, M. M. (2017) Fecal Microbiota Transplantation, Commensal *Escherichia coli* and *Lactobacillus johnsonii* Strains Differentially Restore Intestinal and Systemic Adaptive Immune Cell Populations Following Broad-spectrum Antibiotic Treatment. *Front Microbiol* 8, 2430
51. Lamouse-Smith, E. S., Tzeng, A., and Starnbach, M. N. (2011) The intestinal flora is required to support antibody responses to systemic immunization in infant and germ free mice. *PLoS One* 6, e27662
52. Lynn, M. A., Tumes, D. J., Choo, J. M., Sribnaia, A., Blake, S. J., Leong, L. E. X., Young, G. P., Marshall, H. S., Wesselingh, S. L., Rogers, G. B., and Lynn, D. J. (2018) Early-Life Antibiotic-Driven Dysbiosis Leads to Dysregulated Vaccine Immune Responses in Mice. *Cell Host Microbe* 23, 653-660 e655
53. Scott, N. A., Andrusaite, A., Andersen, P., Lawson, M., Alcon-Giner, C., Leclaire, C., Caim, S., Le Gall, G., Shaw, T., Connolly, J. P. R., Roe, A. J., Wessel, H., Bravo-Blas, A., Thomson, C. A., Kastele, V., Wang, P., Peterson, D. A., Bancroft, A., Li, X., Grencis, R., Mowat, A. M., Hall, L. J., Travis, M. A., Milling, S. W. F., and Mann, E. R. (2018) Antibiotics induce sustained dysregulation of intestinal T cell immunity by perturbing macrophage homeostasis. *Sci Transl Med* 10
54. Beli, E., Yan, Y., Moldovan, L., Vieira, C. P., Gao, R., Duan, Y., Prasad, R., Bhatwadekar, A., White, F. A., Townsend, S. D., Chan, L., Ryan, C. N., Morton, D., Moldovan, E. G., Chu, F. I., Oudit, G. Y., Derendorf, H., Adorini, L., Wang, X. X., Evans-Molina, C., Mirmira, R. G., Boulton, M. E., Yoder, M. C., Li, Q., Levi, M., Busik, J. V., and Grant, M. B. (2018) Restructuring of the Gut Microbiome by Intermittent Fasting Prevents Retinopathy and Prolongs Survival in db/db Mice. *Diabetes* 67, 1867-1879
55. Li, G., Xie, C., Lu, S., Nichols, R. G., Tian, Y., Li, L., Patel, D., Ma, Y., Brocker, C. N., Yan, T., Krausz, K. W., Xiang, R., Gavrilova, O., Patterson, A. D., and Gonzalez, F. J. (2017) Intermittent Fasting Promotes White Adipose Browning and Decreases Obesity by Shaping the Gut Microbiota. *Cell Metab* 26, 672-685 e674
56. Cignarella, F., Cantoni, C., Ghezzi, L., Salter, A., Dorsett, Y., Chen, L., Phillips, D., Weinstock, G. M., Fontana, L., Cross, A. H., Zhou, Y., and Piccio, L. (2018) Intermittent Fasting Confers Protection in CNS Autoimmunity by Altering the Gut Microbiota. *Cell Metab* 27, 1222-1235 e1226
57. Song, J. X., Ren, H., Gao, Y. F., Lee, C. Y., Li, S. F., Zhang, F., Li, L., and Chen, H. (2017) Dietary Capsaicin Improves Glucose Homeostasis and Alters the Gut Microbiota in Obese Diabetic ob/ob Mice. *Front Physiol* 8, 602
58. Van Hul, M., Geurts, L., Plovier, H., Druart, C., Everard, A., Stahlman, M., Rhimi, M., Chira, K., Teissedre, P. L., Delzenne, N. M., Maguin, E., Guilbot, A., Brochot, A., Gerard, P., Backhed, F., and Cani, P. D. (2018) Reduced obesity, diabetes, and steatosis upon cinnamon and grape pomace are associated with changes in gut microbiota and markers of gut barrier. *Am J Physiol Endocrinol Metab* 314, E334-E352
59. Franco-de-Moraes, A. C., de Almeida-Pititto, B., da Rocha Fernandes, G., Gomes, E. P., da Costa Pereira, A., and Ferreira, S. R. G. (2017) Worse inflammatory profile in omnivores than in vegetarians associates with the gut microbiota composition. *Diabetol Metab Syndr* 9, 62.

The invention claimed is:
1. A method of ameliorating the growth or spread of a tumor comprising the steps of: a) selecting a patient suffering from a tumor; b) administering a combination of i) an inhibitor of NR2F6 nucleic acid selected from the group consisting of: a nucleic acid capable of inducing RNA interference and an antisense oligonucleotide and ii) a cannabidiol to said patient in an amount to ameliorate the growth or spread of said tumor.
2. The method of claim 1, wherein said inhibitor of NR2F6 nucleic acid is a nucleic acid capable of inducing RNA interference.
3. The method of claim 2, wherein said nucleic acid capable of inducing RNA interference is a short hairpin RNA.
4. The method of claim 2, wherein said nucleic acid capable of inducing RNA interference is a short interfering RNA.
5. The method of claim 2, wherein said nucleic acid capable of inducing RNA interference is a miRNA.
6. The method of claim 1, wherein said inhibitor of NR2F6 nucleic acid is an antisense oligonucleotide.
7. The method of claim 1, wherein said inhibitor of NR2F6 nucleic acid is administered intralymphatically.
8. The method of claim 7, wherein said administration is perilymphatic administration.
9. The method of claim 8, wherein perilymphatic administration is performed by a subcutaneous injection proximal to an area that drains into one or a plurality of lymph nodes.
10. The method of claim 9, wherein said perilymphatic administration is performed by a intradermal injection proximal to an area that drains into one or a plurality of lymph nodes.
11. The method of claim 9, wherein said area that drains into one or a plurality of lymph nodes is identified by a visualization means.
12. The method of claim 11, wherein said visualization means is comprised of lymphangiography.
13. A method of ameliorating the growth or spread of a tumor comprising the steps of: a) selecting a patient suffering from a tumor; b) surgically removing the tumor or a portion thereof from said patient; and c) after the surgical removal, administering a combination of i) an inhibitor of NR2F6 nucleic acid selected from the group consisting of: a nucleic acid capable of inducing RNA interference and an antisense oligonucleotide and ii) a cannabidiol to said patient in an amount to ameliorate the growth or spread of said tumor.

14. The method of claim 13, wherein said inhibitor of NR2F6 nucleic acid is a nucleic acid capable of inducing RNA interference.

15. The method of claim 13, wherein said inhibitor of NR2F6 nucleic acid is an antisense oligonucleotide.

16. The method of claim 13, wherein said inhibitor of NR2F6 nucleic acid is administered intralymphatically.

17. The method of claim 16, wherein said administration is perilymphatic administration.

18. The method of claim 17, wherein perilymphatic administration is performed by a subcutaneous injection proximal to an area that drains into one or a plurality of lymph nodes.

19. The method of claim 18, wherein said area that drains into one or a plurality of lymph nodes is identified by a visualization means.

\* \* \* \* \*